(12) United States Patent
Mihan et al.

(10) Patent No.: US 7,649,063 B2
(45) Date of Patent: Jan. 19, 2010

(54) SUPPORTED METAL ALKYL COMPOUND AND ITS PREPARATION

(75) Inventors: Shahram Mihan, Bad Soden (DE);
Rosendorfer Philipp, Neustadt (DE);
Rainer Karer, Kaiserslautern (DE);
Martin Schneider, Kelkheim (DE);
Peter Eck, Bad Dürkheim (DE)

(73) Assignee: Basell Polyolefine GmbH, Wesseling (DE)

( * ) Notice: Subject to any disclaimer, the term of this patent is extended or adjusted under 35 U.S.C. 154(b) by 277 days.

(21) Appl. No.: 10/575,731

(22) PCT Filed: Oct. 9, 2004

(86) PCT No.: PCT/IB2004/011316

§ 371 (c)(1),
(2), (4) Date: Aug. 18, 2008

(87) PCT Pub. No.: WO2005/039763

PCT Pub. Date: May 6, 2005

(65) Prior Publication Data

US 2008/0306224 A1    Dec. 11, 2008

Related U.S. Application Data

(60) Provisional application No. 60/518,427, filed on Nov. 6, 2003.

(30) Foreign Application Priority Data

Oct. 15, 2003   (DE) ................................ 103 48 624

(51) Int. Cl.
*C08F 2/34*   (2006.01)
*B01J 20/22*  (2006.01)
*B01J 20/32*  (2006.01)
*C07C 7/12*   (2006.01)

(52) U.S. Cl. ................ 526/159; 526/123.1; 526/129; 526/156; 502/401; 585/830; 260/665 R; 260/665 B

(58) Field of Classification Search ................. 526/173, 526/183, 185, 190, 901, 123.1, 129, 156, 526/159; 502/401; 585/830; 260/665 R, 260/665 B
See application file for complete search history.

(56) References Cited

U.S. PATENT DOCUMENTS

| 3,709,853 A |   | 1/1973 | Karapinka ............. 260/88.2 D |
|---|---|---|---|
| 4,035,560 A |   | 7/1977 | Caumartin et al. .......... 526/124 |
| 4,370,456 A |   | 1/1983 | George ....................... 526/125 |
| 4,532,311 A |   | 7/1985 | Fulks et al. ................... 526/62 |
| 4,614,729 A | * | 9/1986 | Crawford et al. ............ 502/401 |
| 4,764,056 A |   | 8/1988 | Zentgraf et al. ............... 406/68 |
| 5,446,001 A |   | 8/1995 | Gurtzgen ..................... 502/151 |
| 5,661,098 A |   | 8/1997 | Harrison et al. ............. 502/120 |

FOREIGN PATENT DOCUMENTS

| DE | 2623693 | 12/1976 |
|---|---|---|
| EP | 0226935 | 7/1987 |
| EP | 0560128 | 9/1993 |
| GB | 1500868 | 2/1978 |
| JP | 53011982 | 2/1978 |
| SU | 0409723 | 6/1974 |
| WO | 9510542 | 4/1995 |
| WO | 9704015 | 2/1997 |
| WO | 0002929 | 1/2000 |
| WO | 0031090 | 6/2000 |

* cited by examiner

*Primary Examiner*—Fred M Teskin
(74) *Attorney, Agent, or Firm*—William R. Reid; Jonathan L. Schuchardt

(57) ABSTRACT

Pulverulent solid which consists essentially of at least one metal alkyl compound bound chemically and/or physically to a finely divided, porous, mechanically stable and chemically inert support, has a proportion by weight of metal alkyl compound of at least 5% by weight, based on the support, and has an angle of repose, determined in accordance with ISO 4324, of up to 48°. The solid allows trouble-free metering as active component into a reactor.

11 Claims, No Drawings

SUPPORTED METAL ALKYL COMPOUND AND ITS PREPARATION

CROSS-REFERENCE TO RELATED APPLICATIONS

This application is the U.S. national phase of International Application PCT/EP2004/011316, filed Oct. 9, 2004, claiming priority to German Patent Application 10348624.0 filed Oct. 15, 2003, and the benefit under 35 U.S.C. 119(e) of U.S. Provisional Application No. 60/518,427, filed Nov. 6, 2003; the disclosures of International Application PCT/EP2004/011316, German Patent Application 10348624.0 and U.S. Provisional Application No. 60/518,427, each as filed, are incorporated herein by reference.

FIELD OF THE INVENTION

The present invention relates to a pulverulent solid consisting essentially of at least one metal alkyl compound which is chemically and/or physically bound to a finely divided, porous, mechanically stable and chemically inert support. It further provides a process for preparing this solid and to its use in a polymerization process.

BACKGROUND OF THE INVENTION

Solids of this type are known, for example, from the Japanese published specification JP-A-53-011 982 or from DE-A-26 23 693.

The solid described in JP-A-53-011 982 is magnesium oxide, zinc oxide, silica gel, magnesium hydroxide, aluminum silicate or magnesium silicate which has been reacted with triethylaluminum, tri-n-octylaluminum, diethylaluminum hydride or isobutylaluminum dihydride at from 50 to 100° C. in hexane or decane. The resulting solids or supported aluminum compounds are used as activators for Phillips catalysts comprising chromium oxide in ethylene polymerization. For the aluminum alkyl compounds to be able to display their known activation effect, they have to react with the chromium oxide of the Phillips catalysts. It is therefore a physical requirement that the solid of JP-A-53-011 982 contains only a very small amount, if any, of immobilized aluminum alkyls, since otherwise the mass transfer between the solid and the Phillips catalyst which is essential for activation would no longer take place. Nothing is said in JP-A-53-011 982 about a purifying effect of the solid.

The solid described in DE-A-26 23 693 is likewise based on supports such as alumina, hydrated alumina, silicic acid, aluminum silicate and magnesium silicate and, in addition, calcium carbonate, magnesium carbonate or a polyolefin powder which have been impregnated with at least one liquid aluminum alkyl compound having a vapor pressure of less than 1 mm/80° C., e.g. tri-n-octylaluminum. These solids are used as cocatalysts for the (co)polymerization of α-monoolefins in the gas phase by means of Ziegler or Phillips catalysts comprising transition metals.

EP-A-560128 discloses a solid which contains metal alkyl groups and in which the metal alkyls are all bound to the surface of the support. Although this has the advantage that it reduces the interactions with the polymerization catalyst, the supported metal alkyl compounds obtained in this way have, like all other previously known solids comprising metal alkyls, the disadvantage that they easily become conglutinated when being metered into the reaction, in particular when using long, narrow lines, and are therefore not very suitable for metering into a gas-phase fluidized-bed reactor.

SUMMARY OF THE INVENTION

It is an object of the present invention to overcome the abovementioned disadvantages of the prior art and to provide a supported metal alkyl compound which allows trouble-free metering into a reactor, in particular into a gas-phase fluidized-bed reactor.

We have found that this object is achieved by a novel solid which is based on a metal alkyl compound bound chemically and/or physically to a finely divided, porous and mechanically stable support, has a metal alkyl content of more than 5% by weight and has an angle of repose, determined in accordance with ISO 4324, of not more than 48°.

DETAILED DESCRIPTION OF THE INVENTION

Due to its excellent powder flow properties, the solid of the present invention is suitable for metering through even narrow and/or long feed lines without blockages occurring.

In the following, this novel solid based on the metal alkyls and the supports will in the interest of brevity be referred to as supported metal alkyl.

It is important, firstly, that the supported metal alkyl of the present invention has an angle of repose determined in accordance with ISO 4324 of not more than 48°. The angle of repose is a suitable measure for the powder flow of the supported metal alkyl and thus also a measure of its suitability in respect of metering.

Secondly, the supported metal alkyl has at least 5% by weight, preferably from 10 to 40% by weight, particularly preferably from 15 to 30% by weight (based on the support), of the metal alkyl compound on the surface of the support. The solids of the present invention thus contain an amount of metal alkyl compound which is significantly above that corresponding to saturation of the free bonding sites of the solid, so that metal alkyl which is not chemically bound is also present on the support surface. According to the present invention, the term physical bonding refers to any attractive, nonchemical interaction which is able to hold the metal alkyl on the surface of the support.

The main basis of the supported metal alkyl is formed by a monovalent, divalent or higher-valent metal alkyl. Accordingly, all metal alkyls of 1-, 2-, 3-, 4- and 5-valent metals, but in particular the alkyls of 2-, 3- and 4-valent metals, are suitable. Examples of well-suited metal alkyls are the alkyl compounds of beryllium, magnesium, calcium, strontium, barium, zinc, boron, aluminum, gallium, indium, thallium, tin and lead. Among these, the alkyl compounds of boron, aluminum and zinc are particularly advantageous and are therefore very particularly preferably used. The alkyl compounds of aluminum in turn offer very particular advantages for the preparation of the solid of the present invention and are therefore accorded special importance and are very particularly preferably employed.

In general, the alkyl groups of the metal alkyls have from 1 to 20 carbon atoms and may also be substituted as long as the substituent is compatible with the support and the intended use. Alkyl groups having from 2 to 8 carbon atoms, e.g. ethyl, propyl, isopropyl, n-butyl, isobutyl, n-pentyl, n-hexyl, heptyl, octyl and 2-methylhexyl and also cyclohexyl and methylcyclohexyl are very particularly advantageous and are therefore very particularly preferably used. Apart from fully alkylated metal alkyl compounds, it is also possible to use partially alkylated metal alkyl compounds, with possible further substituents being, for example, halogens, in particular chlorine and iodine, hydrides or alkoxy groups.

Examples of metal alkyls which are preferably used for preparing the solid of the present invention are trimethylaluminum, triethylaluminum, tripropylaluminum tributylaluminum, triisobutylaluminum, trihexylaluminum, trioctylaluminum, tridodecylaluminum diethylaluminum chloride, diethylaluminum hydride, ethylaluminum sesquichloride ethylaluminum dichloride, diisobutylaluminum chloride, isobutylaluminum dichloride, diethylaluminum iodide, dipropylaluminum chloride, diisobutylaluminum hydride, diethylaluminum ethoxide, dimethylalumnium chloride, methylaluminum sesquichloride, diethylzinc, triethylboron, butyloctylmagnesium and also partially hydrolyzed metal alkyls such as methylaluminoxane (MAO) or isobutylaluminoxane (IBAO). Particular preference is given to triethylaluminum, triisobutylaluminum and trihexylaluminum, diethylzinc and diethylaluminum ethoxide. The metal alkyls are compounds which are known per se and are commercially available.

The further important basis of the supported metal alkyl is formed by the finely divided, porous and mechanically stable support. This support or the particles of which it consists is/are abrasion resistant, which is very important for use of the solid of the present invention in a fluidized or stirred gas phase or in a suspension with turbulent flow, and the support is also not damaged under its own weight during storage.

The support to be employed according to the present invention preferably bears, in the unladen state, i.e. in the state free of metal alkyl, functional groups on its surface which can effect chemical and/or physical bonding between the metal atoms of the metal alkyl and the surface of the support. Furthermore, it is important for the solid of the present invention that only the surface of the support reacts with the metal alkyls and the remainder of the support is chemically inert toward these.

Possible supports include both polymeric organic solids and polymeric and/or crystalline inorganic solids.

Inorganic oxides suitable as supports may be found among the oxides of elements of groups 2, 3, 4, 5, 13, 14, 15 and 16 of the Periodic Table of the Elements. Preference is given to oxides or mixed oxides of the elements calcium, aluminum, silicon, magnesium, titanium, zirconium or hafnium and also corresponding oxide mixtures. Other inorganic oxides which can be used either alone or in combination with the above-mentioned oxidic supports are, for example, $ZrO_2$ or $B_2O_3$. Preferred oxides are silicon dioxide, in particular in the form of a silica gel or a pyrogenic silica, or aluminum oxide. A preferred mixed oxide is, for example, calcined hydrotalcite. Further inorganic support materials which may be mentioned are, for example, magnesium chloride, aluminum oxide hydrate, aluminum phosphate or metal silicates.

In general, inorganic supports which, like silicates or aluminosilicates, have a porous structure with a large surface area have a mean particle size of from 1 µm to 1 mm, preferably from 10 to 100 µm, in particular from 20 to 70 µm. The support advantageously has a BET surface area of from 10 to 1000 $m^2/g$, preferably from 50 to 500 $m^2/g$ and in particular from 200 to 400 $m^2/g$. It is also advantageous for its pore volume to be from 0.1 to 5 ml/g, preferably from 0.8 to 3.5 ml/g, particularly preferably from 0.9 to 2.5 ml/g. Exceptions are supports whose surfaces are formed only by means of swelling, for example in the case of sheet silicates or hydrotalcites.

The inorganic support can be subjected to a thermal treatment, for example to remove adsorbed water. Such a drying treatment is in general carried out at from 80 to 300° C., preferably from 100 to 200° C., preferably under reduced pressure and/or in a stream of inert gas, for example nitrogen or argon. The inorganic support can also be calcined, in which case the concentration of OH groups on the surface can then be set and the structure of the solid can possibly be altered by treatment at from 200 to 1000° C.

The inorganic support material can also be modified chemically. For example, treatment of silica gel with $NH_4SiF_6$ leads to fluorination of the silica gel surface or treatment of silica gels with silanes containing nitrogen-, fluorine- or sulfur-containing groups gives correspondingly modified silica gel surfaces. Further treatment methods are described in WO 00/31090.

Examples of organic solids which can be used as supports are modified and unmodified cellulose and starch, modified and unmodified lignin, synthetic polymers which contain carboxylic acid, sulfonic acid, phosphonic acid, acid phosphoric ester, hydroxy and/or primary and/or secondary amino groups and are based on polyethylene and ethylene copolymers, polypropylene and propylene copolymers, vinyl chloride copolymers, polystyrene and styrene copolymers, polyphosphazenes, polyamides, polycarbonates, polyalkylene terephthalates, polyphenylene oxides, polysulfones, polyphenylene sulfides, polyaryl sulfones, polyether sulfones, polyaryl ethers, phenol-formaldehyde resins (phenolic resins), urea-formaldehyde resins (amino resins), melamine-formaldehyde resins, melamine-phenol-formaldehyde resins, silicones, polyimides, epoxy resins or crosslinked polyurethanes. It is also possible to use functionalized polymeric supports, e.g. supports based on polystyrenes. Preferred organic support materials are finely divided polymer powders, for example powders composed of polyolefins such as polyethylene or polypropylene or of polystyrene.

According to the present invention, the supported metal alkyl consists essentially of the two above mentioned components metal alkyl compound and support, with small amounts of additional components also being able to be present. Such additional components can be additives or auxiliaries of any type, for example antistatics.

To obtain the particularly good powder flow properties of the supported metal alkyl, it is advantageously prepared from the metal alkyls and supports described in detail above using the process of the present invention. According to this, the pulverulent solid is obtainable by firstly drying the support to a water content below 3% by weight, preferably 2% by weight, particularly preferably 1% by weight, if the original water content is above this, and then bringing the metal alkyl compound into contact with the support in a solvent having a boiling point which is not above 30° C., followed by removal of the solvent so that the supported alkyl compound remains and a particularly free-flowing pulverulent solid is obtained.

For the present purposes, the water content is the total content of hydroxyl groups, expressed as water, which are able to react with the metal alkyl. The water content can be determined, for example, by titration with the metal alkyl itself.

As solvent to be used in the process of the present invention, it is possible to employ any liquid which is inert toward the metal alkyl compound and has a boiling point less than or equal to 30° C. Preference is given to solvents which are inert toward metal alkyl compounds and have a boiling point in the range from 10 to 30° C. Particular preference is given to isopentane, which has a boiling point of 28° C.

Particularly good results are achieved when the support is firstly suspended in the solvent, in particular isopentane, and the metal alkyl compound is subsequently added in diluted form. As an alternative, the metal alkyl compound can be dissolved beforehand in the isopentane.

The solids of the present invention, in particular those obtained by the process of the present invention, are mechanically stable and are very suitable for the purification of gaseous substances and also of chemical reactors in which air- and/or water-sensitive substances are reacted with one another. They have the advantage over other purifying agents that they eliminate a wide variety of contaminants even in the ppm range, after which they can easily be separated off again from the gaseous substances and be taken from the reactors again.

Substances which are particularly suitable for purification by the solids of the present invention include all inert gases, hydrogen and also polymerizable monomers containing ethylenically unsaturated groups. The reactors are, in particular, plants for the (co)polymerization of such monomers. Here, the solids of the present invention are especially suitable for removing impurities in plants which are intended for the (co)polymerization of olefins in the fluidized or stirred gas phase and contain polymer particles being mixed.

The present invention further provides a process for preparing homopolymers and copolymers of α-olefins in a gas-phase fluidized-bed reactor, in which the α-olefin is (co)polymerized in a polymerization zone of the gas-phase fluidized-bed reactor at from 30 to 125° C. and pressures of from 1 to 100 bar in the gas phase in a mixed bed of finely divided polymer in the presence of a catalyst comprising a transition metal and using the pulverulent solid of the present invention and discharging the resulting (co)polymers from the reactor.

In this process for preparing homopolymers and copolymers of α-olefins, the monomer or monomers concerned is/are fed continuously or discontinuously into the reactor in a known manner. For this purpose, it is possible to use all customary and known catalysts, in particular Phillips, Ziegler and single-site catalysts such as metallocene catalysts as are described, for example, in the prior art discussed at the outset and in U.S. Pat. No. 4,532,311 or U.S. Pat. No. 3,709,853. Among metallocene catalysts, supported chromium(II) compounds such as bis(cyclopentadienyl)chromium(II) are particularly advantageous because they can be used directly for the (co)polymerization without an additional activation step and without addition of cocatalysts. Accordingly, the (co)polymerization can be carried out either in the presence or absence of a cocatalyst. Possible cocatalysts are essentially all the abovementioned metal alkyls, but in particular the alkyl compounds of aluminum, and also the supported cocatalysts mentioned at the outset. In addition, a finely divided, inert solid which is free of metal alkyls can also be present in the (co)polymerization. Further additives which can, if required, be metered into the reactor include molecular weight regulators such as hydrogen and antistatics (cf. U.S. Pat. No. 4,532,311). The (co)polymerization can be carried out in the fluidized or stirred gas phase in a mixed bed of finely divided (co)polymer. Depending on whether this process is carried out continuously or batchwise, the resulting (co)polymers are discharged continuously from the reactor or taken from the reactor after the reaction has ended.

Furthermore, the metal alkyl supported according to the present invention can also be used, in particular for the removal of impurities, in a multizone reactor as is described, for example, in WO 97/04015 or WO 00/02929.

To meter the supported metal alkyls of the present invention into a gas-phase fluidized-bed reactor for the polymerization of ethylene, it is possible to use, for example, the discontinuous metering apparatus described in EP-A-226935.

The solid of the present invention can be introduced into the plants or reactors before carrying out these processes in order to free the reactor of oxygen, water and other interfering compounds. Here, the solid of the present invention displays its excellent purifying action. The solid of the invention can, however, also be introduced during the (co)polymerization to influence the time-activity behavior. For the purposes of the present invention, the time-activity behavior is the change in activity of the catalyst used as a function of time. This can be altered by means of the supported metal alkyls of the present invention. Thus, for example, in the case of Phillips catalysts the reduction of chromium(VI) which is necessary for activation takes a relatively long time when it is brought about by means of ethylene. In contrast, when unsupported metal alkyls such as aluminum alkyls are used, the catalyst starts acting undesirably quickly. The use of supported metal alkyls, on the other hand, makes it possible to achieve a gentle but nevertheless rapid commencement of the reaction within a few minutes.

EXAMPLES

Various metal alkyl compounds were supported and their powder flow behavior was determined.

The method of ISO 4324 was used to determine the powder flow. ISO 4324 is a standard which is actually intended for testing the angle of repose of surfactants in powder or granule form, but can also be applied to other powder and granulated materials having comparable properties. The determination of the angle of repose was carried out under an inert atmosphere.

The powder flow of the pulverulent solid is better the smaller the angle of repose. The angles of repose were, in the interests of simplicity, divided into the following powder flow classes:

| Angle of repose [°] | Powder flow class | Assessment |
|---|---|---|
| up to 44 | 1 | very good |
| 44-46 | 2 | good |
| 46-48 | 3 | slightly sticky |
| 48-50 | 4 | poor |
| above 50 | 5 | very poor |

Example 1

The silica gel (SG 332, pore volume: 1.8 ml/g, mean particle size: 50 μm, specific surface area determined by the BET method: 325 m$^2$/g) was firstly heated at 250° C. for 6 hours under an argon atmosphere. The water content was determined volumetrically by titration of the OH groups with triethylaluminum, giving a value of 1.4% by weight. 33.5 g of the dried silica gel were subsequently suspended in 220 ml of isopentane under a protective gas atmosphere in a 500 ml flask.

10.05 g (30% by weight based on the support) of undiluted trihexylaluminum were then slowly added dropwise to this suspension. As a result of the exothermic reaction, the temperature rose from 12° C. to 27° C. After the trihexylaluminum had been added, the mixture was stirred at not more than 30° C. for another 1 hour and the isopentane was removed at room temperature under reduced pressure.

As can be seen from table 1, a fine product of powder flow class 1 having very good powder flow was obtained.

Examples 2, 3

Example 1 was repeated using 50% by weight and 10% by weight of trihexylaluminum. Products of powder flow classes 2 and 1 having good to very good powder flow were likewise obtained.

Comparative Example C4

Example 1 was repeated using 4% by weight. A supported metal alkyl compound of powder flow class 4 which displayed poor flow was obtained; this is unsuitable for use in the metering apparatus for the gas-phase fluidized-bed reactor.

Comparative Examples C5, C6, C7

Example 1 was modified in that application to the support was carried out using heptane, hexane or pentane instead of isopentane as solvent. Supported metal alkyl compounds of powder flow class 4 or 5 which displayed very poor flow were obtained in each case; these are unsuitable for use in the metering apparatus for the gas-phase fluidized-bed reactor.

Example 8

Example 1 was modified in that the pretreatment of the support comprised a calcination at 750° C. A supported metal alkyl compound of powder flow class 1 which displayed very good flow was obtained.

Example 9

Example 1 was modified in that the pretreatment of the support comprised a calcination at 800° C. and the proportion of metal alkyl compound was 42.9% by weight, based on the support. A supported metal alkyl compound of powder flow class 1 was obtained.

Example 10

Example 1 was carried out using triethylaluminum (TEA) as metal alkyl compound. A supported metal alkyl compound of powder flow class 1 was obtained.

Example 11

Example 1 was carried out using triethylaluminum (TEA) as metal alkyl compound. The thermal pretreatment of the support was omitted. A supported metal alkyl compound of powder flow class 2 was obtained.

Examples 12, 13, 14

Example 1 was repeated using diethylzinc (DEZ), triisobutylaluminum (TIBA) or diethylaluminum ethoxide (DEALOX) as metal alkyl compound. Metal alkyl compounds of powder flow class 2 were obtained.

TABLE 1

| Example | Metal alkyl | Pretreatment of supports [° C.] | Amount of metal alkyl [% by weight] * | Solvent | Powder flow class |
|---|---|---|---|---|---|
| 1 | THA | 250 | 30 | isopentane | 1 |
| 2 | THA | 250 | 50 | isopentane | 1 |
| 3 | THA | 250 | 10 | isopentane | 2 |
| C4 | THA | 250 | 4 | isopentane | 4 |
| C5 | THA | 250 | 30 | heptane | 5 |
| C6 | THA | 250 | 30 | hexane | 5 |
| C7 | THA | 250 | 30 | pentane | 4-5 |
| 8 | THA | 750 | 30 | isopentane | 1 |
| 9 | THA | 800 | 42.9 | isopentane | 1 |
| 10 | TEA | 250 | 30 | isopentane | 1 |
| 11 | TEA | none | 30 | isopentane | 2 |
| 12 | DEZ | 250 | 30 | isopentane | 2 |
| 13 | TIBA | 250 | 30 | isopentane | 2 |
| 14 | DEALOX | 250 | 30 | isopentane | 1 |

* based on the support

We claim:

1. A pulverulent solid consisting essentially of at least one metal alkyl compound bound chemically and/or physically to a finely divided, porous, mechanically stable and chemically inert support and which has a proportion of metal alkyl compound of 10% to 40% by weight, based on the support, and an angle of repose, determined in accordance with ISO 4324, of up to 48°.

2. The pulverulent solid as claimed in claim 1, wherein the at least one metal alkyl compound is selected independently from the group consisting of alkyl compounds of the elements lithium, beryllium, magnesium, calcium, strontium, barium, zinc, boron, aluminum, gallium, indium, thallium, tin and lead.

3. The pulverulent solid as claimed in claim 1, wherein the support is an inorganic support.

4. A process for preparing a pulverulent solid consisting essentially of at least one metal alkyl compound bound chemically and/or physically to a finely divided, porous, mechanically stable and chemically inert support having an original water content, and which has a proportion of metal alkyl compound of 10% to 40% by weight, based on the support, and an angle of repose, determined in accordance with ISO 4324, of up to 48°,
the process comprising the steps:
drying the support to a water content of less than 3% by weight if the original water content is at least 3% by weight;
bringing the metal alkyl compound into contact with the support in an inert solvent having a boiling point of less than 30° C.; and
removing the solvent from the pulverulent solid.

5. The process as claimed in claim 4, wherein the solvent is isopentane.

6. The process as claimed in claim 4, wherein the support is suspended in isopentane and the at least one metal alkyl compound is subsequently added in undiluted form or as a solution in isopentane.

7. The process as claimed in claim 4, wherein the solvent is removed at from 0 to 40° C. and pressures up to 10 000 Pa.

8. A process for preparing homopolymers and copolymers of α-olefins in a gas-phase fluidized-bed reactor, in which the α-olefin is (co)polymerized in a polymerization zone of the gas-phase fluidized-bed reactor at from 30 to 125° C. and pressures of from 1 to 100 bar in the gas phase in a mixed bed of finely divided polymer in the presence of at least one catalyst comprising a transition metal and in the presence of a pulverulent solid, and the resulting (co)polymers are discharged from the reactor, wherein the pulverulent solid consists essentially of at least one metal alkyl compound bound chemically and/or physically to a finely divided, porous, mechanically stable and chemically inert support and which has a proportion of metal alkyl compound of 10% to 40% by weight, based on the support, and an angle of repose, determined in accordance with ISO 4324, of up to 48°.

9. The process as claimed in claim 8, wherein a time-activity behavior of the catalyst used is influenced by means of the solid.

10. The process as claimed in claim 8, wherein the solid is used to remove oxygen, carbon dioxide, water and/or other interfering compounds during start-up of the gas-phase fluidized-bed reactor.

11. The pulverulent solid as claimed in claim 3, wherein the inorganic support is selected from silicon dioxide, aluminum oxide, magnesium oxide or mixtures thereof.

* * * * *